(12) United States Patent
Snell et al.

(10) Patent No.: US 11,690,731 B2
(45) Date of Patent: Jul. 4, 2023

(54) SPINAL INTERBODY WITH COMPRESSIVE FUSION FEATURES

(71) Applicant: Spinal Simplicity, LLC, Overland Park, KS (US)

(72) Inventors: Douglas Snell, Overland Park, KS (US); Annaria Barnds, Roeland Park, KS (US); Adam Rogers, Overland Park, KS (US); Melissa Frock, Larwill, IN (US); Todd Moseley, Olathe, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 176 days.

(21) Appl. No.: 17/201,391

(22) Filed: Mar. 15, 2021

(65) Prior Publication Data

US 2021/0196475 A1 Jul. 1, 2021

Related U.S. Application Data

(63) Continuation of application No. 15/584,732, filed on May 2, 2017, now Pat. No. 10,945,856.

(60) Provisional application No. 62/330,581, filed on May 2, 2016.

(51) Int. Cl.
| | |
|---|---|
| *A61F 2/44* | (2006.01) |
| *A61B 17/70* | (2006.01) |
| *A61F 2/30* | (2006.01) |
| *A61B 17/86* | (2006.01) |
| *A61B 17/84* | (2006.01) |

(52) U.S. Cl.
CPC ........ *A61F 2/4455* (2013.01); *A61B 17/7044* (2013.01); *A61B 17/86* (2013.01); *A61F 2/446* (2013.01); *A61B 17/846* (2013.01); *A61F 2/44* (2013.01); *A61F 2/4425* (2013.01); *A61F 2002/30004* (2013.01); *A61F 2002/30166* (2013.01); *A61F 2002/30266* (2013.01); *A61F 2002/30411* (2013.01); *A61F 2002/30556* (2013.01); *A61F 2002/30579* (2013.01); *A61F 2002/30779* (2013.01); *A61F 2002/30787* (2013.01)

(58) Field of Classification Search
CPC .......... A61F 2/4455; A61F 2/446; A61F 2/44; A61F 2/4425; A61F 2002/30556; A61F 2002/30579; A61F 2002/30787; A61B 17/7044
USPC ........................................... 623/17.11–17.16
See application file for complete search history.

(56) References Cited

U.S. PATENT DOCUMENTS

| | | | |
|---|---|---|---|
| 2005/0049590 A1* | 3/2005 | Alleyne | A61F 2/442 606/279 |
| 2013/0166029 A1* | 6/2013 | Dinville | A61B 17/7076 623/17.16 |

\* cited by examiner

*Primary Examiner* — Marcela I. Shirsat
(74) *Attorney, Agent, or Firm* — Erise IP, P.A.

(57) ABSTRACT

An interbody spacer for a spine includes a housing having a plurality of clearance holes configured to engage bone of the spine. A contact plate including a plurality of apertures is positioned a distance away from the housing configured to engage bone of the spine. A plurality of rivets adjoin the housing and the contact plate. A plurality of springs are included with each spring configured to encircle a respective rivet and translate the distance between the housing and contact plate from a minimum distance to a maximum distance.

20 Claims, 4 Drawing Sheets

SPINAL INTERBODY WITH COMPRESSIVE FUSION FEATURES

CROSS-REFERENCE TO RELATED APPLICATIONS

This patent application is a continuation application claiming priority benefit, with regard to all common subject matter, of U.S. patent application Ser. No. 15/584,732, filed on May 2, 2017 and entitled "SPINAL INTERBODY WITH COMPRESSIVE FUSION FEATURES" ("the '732 application"). The "732 application claims priority benefit, with regard to all common subject matter, of U.S. Provisional Patent Application Ser. No. 62/330,581, filed May 2, 2016, and entitled "SPINAL INTERBODY WITH COMPRESSIVE FUSION FEATURES." The identified earlier-filed patent applications are hereby incorporated by reference in their entirety into the present application.

BACKGROUND OF THE INVENTION

Field of the Invention

This application relates generally to spinal implants, and in particular, intervertebral spacers and fusion cages.

Description of Related Art

Back pain can be caused by a variety of factors including but not limited to the rupture or degeneration of one or more intervertebral discs due to degenerative disc disease, spondylolisthesis, deformative disorders, trauma, tumors and the like. In such cases, pain typically results from compression or irritation of spinal nerve roots arising from reduced spacing between adjacent vertebrae, a damaged disc and or misalignment of the spine resulting from the injury or degeneration.

Common forms of treating such pain include various types of surgical procedures in which a damaged disc may be partially or totally excised. After the disc space is prepared, one or more implants are inserted between the adjacent vertebrae in an effort to restore the natural spacing and alignment between the vertebrae, so as to relieve the compression, irritation or pressure on the spinal nerve or nerves and, thereby, eliminate or significantly reduce the pain that the patient is experiencing. Typically, one or more implants are used together with substances that encourage bone ingrowth to facilitate fusion between adjacent vertebrae and achieve immobilization of adjacent bones. Surgeons insert these intervertebral devices to adjunctively facilitate bone fusion in between and into the contiguous involved vertebrae. This fusion creates a new solid bone mass and provides weight bearing support between adjacent vertebral bodies which acts to hold the spinal segment at an appropriate biomechanically restored height as well as to stop motion in a segment of the spine and alleviate pain.

In the typical procedures described above, the adjacent vertebrae must be distracted apart by a substantial amount in order to allow the surgeon to advance the implant with relatively little resistance along the delivery path. Once positioned, the interbody spacer is secured to the adjacent vertebrae with one or more bone screws. Over time, the interface between the screws and the bone may present some problems of stability. Due to the anatomical structure of the spine and the extreme anatomical forces that are brought to bear on the skeleton and transmitted to the vertebral bodies, the screws securing the interbody spacer to the spine may vibrate or toggle out of position.

Therefore, there is a need to provide a new and improved interbody spacer that resists fasteners, such as bone screws, from being loosened with respect to the implant before migrating out. Furthermore, there is a need for the implant to withstand anatomical forces and be easily implanted.

SUMMARY OF THE INVENTION

It should be appreciated that the present technology can be implemented and utilized in numerous ways, including without limitation as a process, an apparatus, a system, a device, a method for applications now known and later developed. These and other unique features of the technology disclosed herein will become more readily apparent from the following description and the accompanying drawings.

An interbody spacer for a spine includes a housing having a plurality of clearance holes configured to engage bone of the spine. A contact plate including a plurality of apertures is positioned a distance away from the housing configured to engage bone of the spine. A plurality of rivets adjoin the housing and the contact plate. A plurality of springs are positioned with each spring configured to encircle a respective rivet and translate the distance between the housing and contact plate from a minimum distance to a maximum distance.

Each of the plurality of rivets can include a rivet head and a shank extending from the rivet head. The rivet head can be positioned within a respective clearance hole of the housing and the shank can be positioned in a respective aperture of the contact plate. Each of the plurality of springs can be positioned around a respective shank of the rivet between the housing and contact plate.

The spacer can be configured for implanting between bones of the spine with each of the plurality of springs in a compressed state. The minimum distance between the housing and contact plate can be defined by each of the plurality of springs being in a compressed state. The maximum distance between the housing and contact plate can be defined by each of the plurality of springs being in a free length state. The housing can include polymer while the contact plate can include a metal. The housing may also include an internal cavity configured to retain bone graft material therein.

In another embodiment, an interbody spacer for a spine includes a body having an upper surface and a lower surface. Each of the upper and lower surfaces is configured to engage with bone of the spine. A gripping member is positioned within an interior of the body having at least two opposing arms. A compression spring adjoins the arms of the gripping member. The arms extend outwardly from the upper surface and lower surface when the compression spring is in a compressed state and the arms retract inwardly toward the body when the compression spring is decompressed.

Each of the arms can include teeth configured to grip bone of the spine. The gripping member can be generally Y shaped with a base positioned within a first passage of the body and the first arm positioned within a first curved passage and the second arm positioned within a second curved passage. An instrument can be used to insert the spinal interbody with the spring in a compressed state. The body can further include an internal cavity configured to retain bone graft material therein.

In yet another embodiment, an interbody spacer for a spine includes an elongated threaded shaft including a first end and an opposing second end. A first spring loaded ramp is positioned near the first end. A second spring loaded ramp is positioned near the second end. The first and second spring loaded ramps are configured to maintain a minimum distance between bones of the spine The spacer can further include a first driving wedge configured to be threadably engaged with the first end of the shaft and a second driving wedge configured to be threadably engaged with the second end of the shaft. The first and second driving wedges are configured to drive the first and second spring loaded ramps to maintain a maximum distance between bones of the spine.

BRIEF DESCRIPTION OF THE DRAWINGS

So that those skilled in the art to which the subject invention relates will readily understand how to make and use the insertion instrument of the subject technology without undue experimentation, embodiments thereof will be described in detail herein below with reference to the following figures.

DETAILED DESCRIPTION

Figure 1:
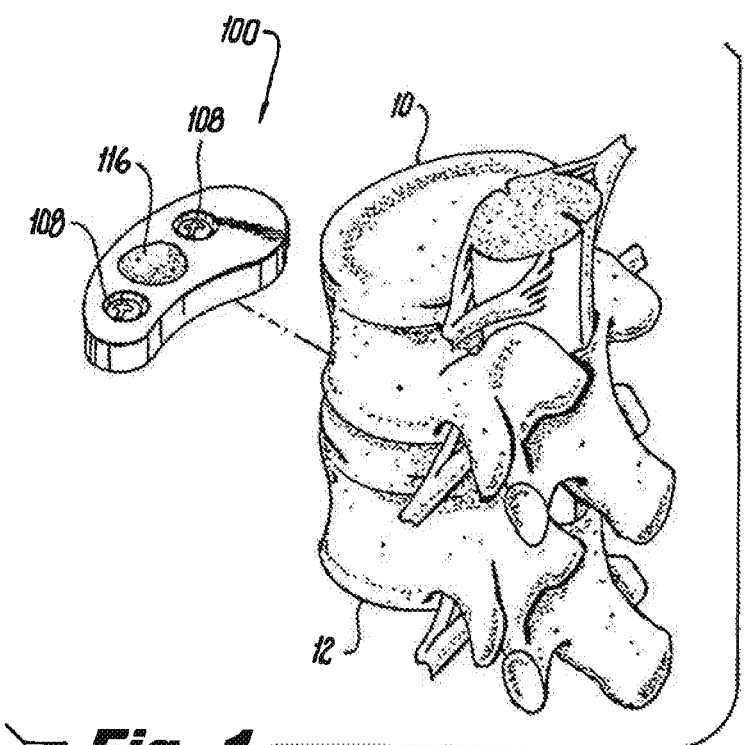
FIG. 1 is a perspective view of a compressive spinal interbody spacer in accordance with a first exemplary embodiment of the subject technology.

The present disclosure overcomes many of the prior art problems associated with interbody designs. The advantages and other features of the instruments and methods disclosed herein will become more readily apparent to those having ordinary skill in the art from the following detailed description of certain preferred embodiments taken in conjunction with the drawings which set forth representative embodiments of the present invention and wherein like reference numerals identify similar structural elements.

All relative descriptions herein such as left, right, up, and down are with reference to the Figures, and not meant in a limiting sense. The illustrated embodiments can be understood as providing exemplary features of varying detail of certain embodiments, and therefore, features, components, modules, elements, and/or aspects of the illustrations can be otherwise combined, interconnected, sequenced, separated, interchanged, positioned, and/or rearranged without materially departing from the disclosed systems or methods. The shapes and sizes of components are also exemplary and unless otherwise specified, can be altered without materially affecting or limiting the disclosed technology.

FIGS. 1-10 illustrate different embodiments of compressive interbody spacers, which could be used in ALIF, XLIF, DLIF, TLIF and PLIF procedures to replace the spinal disc between two vertebrae from C1 to S1.

The purpose of the spacers shown and described herein are to maintain a 5 lb.-15 lb. compressive load on the interbody cage to adjacent vertebral body interface during the patient's healing process. This constant force over the curvature of the adjacent bodies will promote a higher fusion rate than the current offerings.

Figure 2:
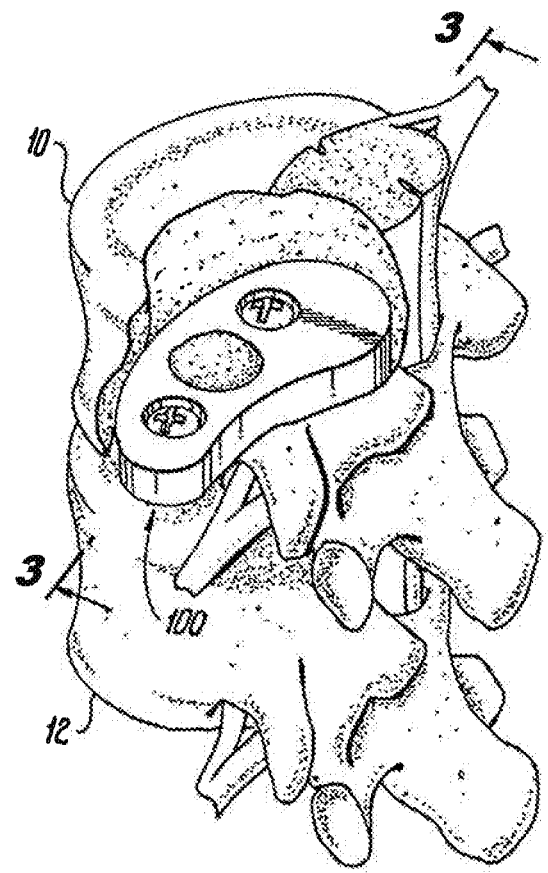
FIG. 2 is a perspective view of the interbody spacer of FIG. 1 positioned between adjacent vertebrae of the spine.

Referring to FIGS. 1-5 a compressive spinal interbody spacer 100 in accordance with a first embodiment is shown. The spacer 100 is shown as a generally concave shape designed to easily and comfortably fit between two adjacent vertebrae 10, 12 of a spine. FIGS. 1 and 2 show the spacer 100 ideally placed within the spine. It will be understood by those skilled in the art that although the additional embodiments of FIGS. 6-10 are not shown within the spine, the embodiments therein can be inserted in the same location to affect the same results.

Figure 3:
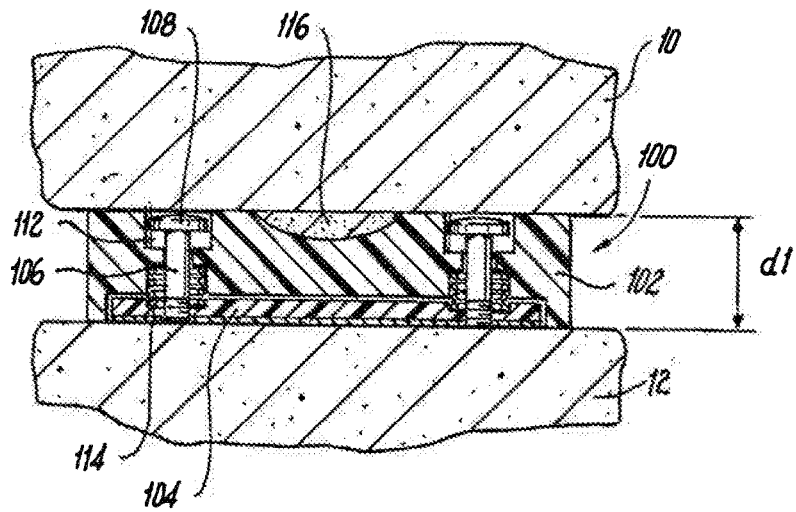
FIG. 3 is a cross-sectional view of interbody spacer of FIG. 1, showing the spacer in a compressed state.
Figure 4:
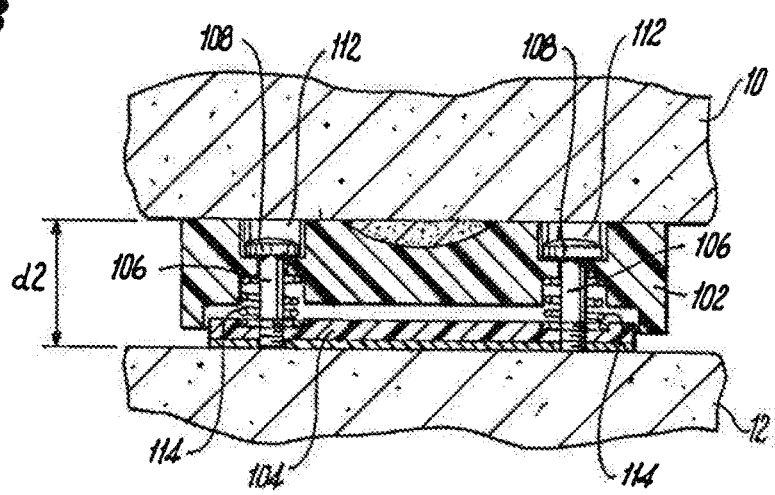
FIG. 4 is a cross-sectional view of interbody spacer of FIG. 1, showing the spacer in an uncompressed state.

With reference to FIG. 3, a cross-sectional view of the spacer 100 is shown in a compressed state between vertebrae 10, 12 of the spine. The spacer 100 includes a housing 102 engaged with bone 10 of the spine and a contact plate 104 engaged with bone 12 of the spine. The housing 102 preferably includes polymer while the contact plate 104 preferably includes metal. The shape and material of this embodiment allows the spacer 100 to conform to the adjacent vertebral body mating faces, such that there is intimate contact across the entire face of the spacer 100. The housing 102 can further include a cavity 116 for placement of bone graft material therein.

The housing 102 and contact plate 104 are joined by a plurality of rivets. Each rivet includes a head 108 and a shank 106 extending from the head 108 designed to join the housing 102 and contact plate 104 together. More specifically, the housing 102 includes a plurality of clearance holes 112 for accepting a respective head 108 of the rivet therein. The contact plate 104 includes a plurality of apertures for accepting a respective shank 106 of the rivet. The clearance holes 112 of the housing are designed to allow the rivet to move longitudinally as the spacer changes from a compressed state (shown in FIG. 3) to an uncompressed state (shown in FIG. 4).

A compressive spring 114 is positioned around each respective rivet shank 106 to alter the spacer 100 from the compressed or uncompressed state. Preferably, the spacer 100 is implanted into the spine in a compressed state. In the compressed state, the housing 102 and contact plate 104 are separated a set minimum distance d1. Over time, as the force of each of the springs 114 release to its natural uncompressed state, the housing 102 and contact plate 104 are slowly separated causing the bones 10, 12 of the spine to also slowly separate. The housing 102 and contact plate 104 are able to separate as far as each of springs 114 extend in the uncompressed state. In other words, the maximum distance d2 between the housing and the contact plate is the free length of spring 114 or the actual length of the spring 114 without any load or force.

Figure 5:
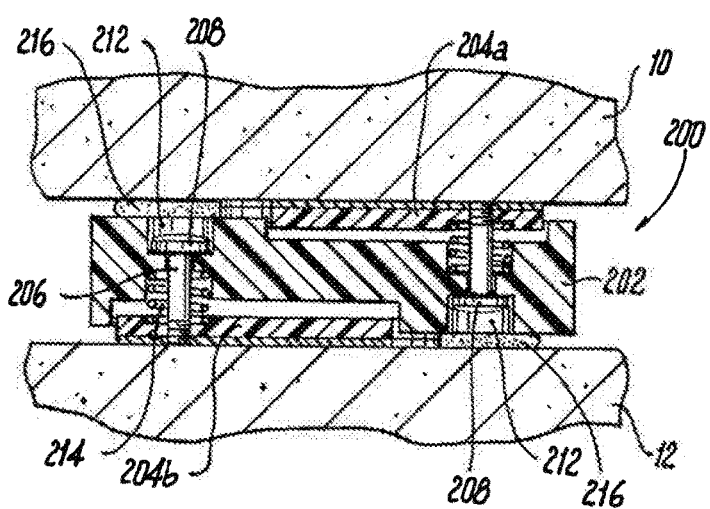
FIG. 5 is a cross-sectional view of another embodiment of a interbody spacer.

FIG. 5 illustrates an alternate embodiment of a spacer 200. In this embodiment, housing 202 is positioned between two contact plates 204a, 204b such that a portion of the housing may contact bone 10, 12, respectively, but contact plates 204a, 204b fully contact bone 10, 12. In this embodiment, at least one rivet is an opposing direction with the remaining rivets. Similar to spacer 100, rivet heads 208 are still maintained within clearance holes 212 with shanks 206 extending through contact plates 204a, 204b, and springs 214 are positioned around each respective shank 206. Further, in this embodiment, a plurality of cavities 216 may be included to enclose bone graft material.

Figure 6:
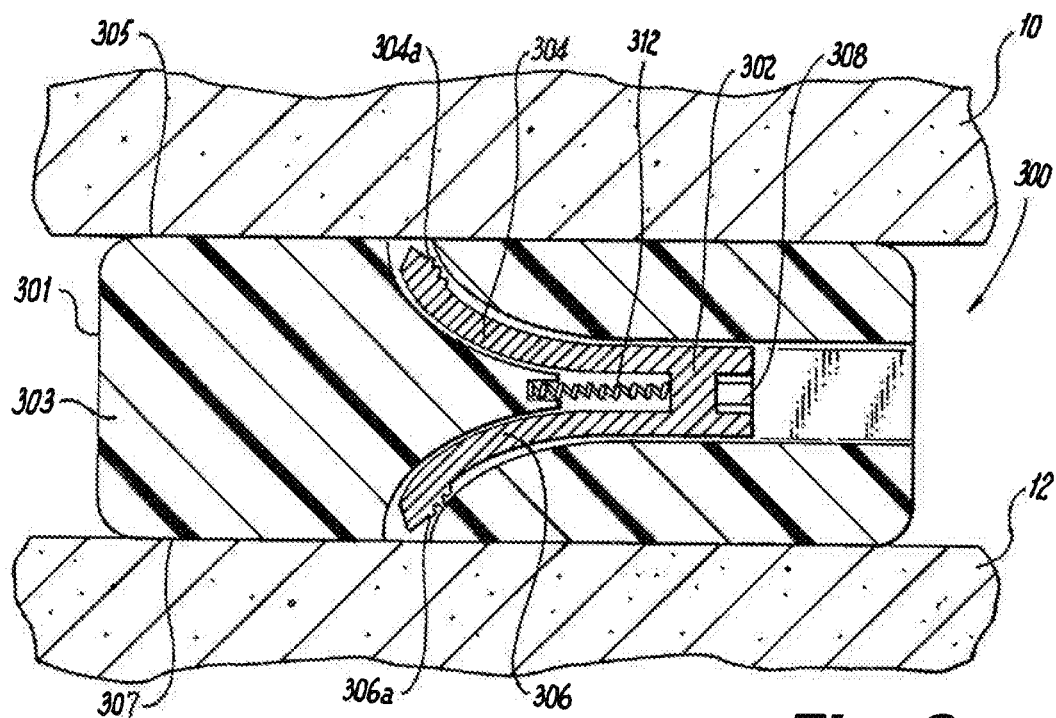
FIG. 6 is a cross-sectional view of a compressive spinal interbody spacer in accordance with a second exemplary embodiment of the subject technology, showing the spacer in an uncompressed state.
Figure 7:
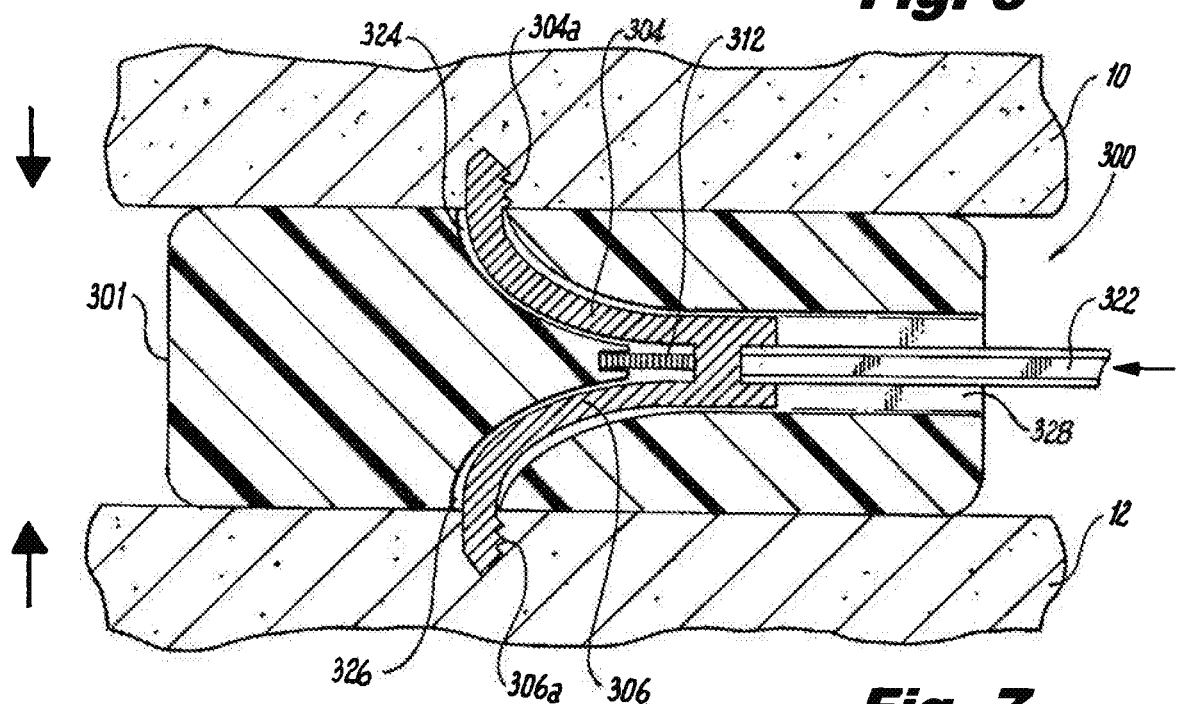
FIG. 7 is a cross-sectional view of the interbody spacer of FIG. 6, showing the spacer in a compressed state.

Referring now to FIGS. 6-7 another embodiment of a compressive spinal interbody spacer 300 in accordance with the present disclosure is shown. As in the previous embodiment, spacer 300 is inserted between bone 10, 12 of a patent's spine to mitigate compression of the spine. Spacer 300 includes a body 301 with an upper surface 305 and a lower surface 307, each surface 305, 307 engages bone 10, 12, respectively, of the spine. A gripping member 302 is positioned within a first passage 328 of an interior portion 303 of the body 301. The gripping member 302 is generally Y shaped with a base and two opposing arms 304, 306 extending outwardly from the base. Each arm 304, 306 includes teeth 304a, 306a at a distal end thereof for gripping onto bone 10, 12 of the spine.

A spring 312 is positioned between the arms 304, 306 of the gripping member 302 and is configured to pull the arms 304, 306 towards the interior 303 of the body 301 as the spring 312 is released from a compressed state to an uncompressed state. More specifically, when the spring 312 is in a fully uncompressed state, as shown in FIG. 6, each of the arms 304, 306 is positioned within respective first and second passages 324, 326. When the spring 312 is in a fully compressed state, as shown in FIG. 7, the arms 304, 306 extend past the respective upper and lower surfaces 305, 307 to contact bone 10, 12 of the spine.

During implantation of the spacer 300 within the spine, an instrument 322 may be used within passage 328 to contact the gripping member 302 through bore 308 to ensure the spring 312 is in a fully compressed state. Once implanted the teeth 304a, 306a of arms 304, 306 contact and grasp bone 10, 12 of the spine adjacent the upper and lower surfaces 305, 307. When the instrument 322 is removed the spring 312 over time slowly returns to its natural uncompressed state. As the spring 312 returns to an uncompressed state, the arms 304, 306 slowly draw the bone 10, 12 towards the body 301. This allows for the spacer 300 and in particular, the gripping member 302 to consistently and gently pull the bone 10, 12 towards the spacer 300 such that the compressive force on the spine is evenly distributed across the spacer 300 to reduce pain and further damage.

Figure 8:
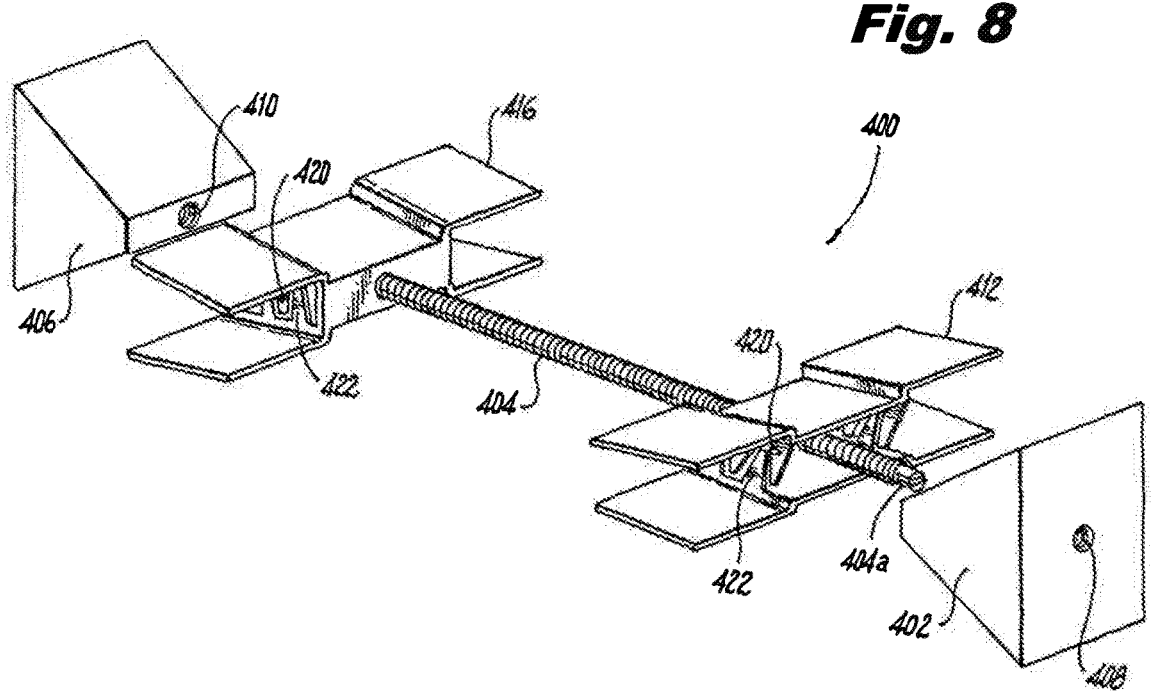
FIG. 8 is an exploded view of a compressive spinal interbody spacer in accordance with a third exemplary embodiment of the subject technology.
Figure 9:
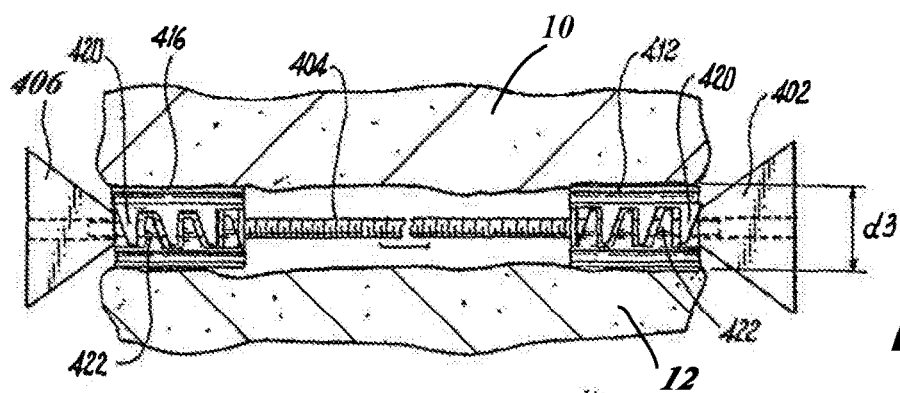
FIG. 9 is a cross-sectional view of the interbody spacer of FIG. 8, showing the spacer in a compressed state.
Figure 10:
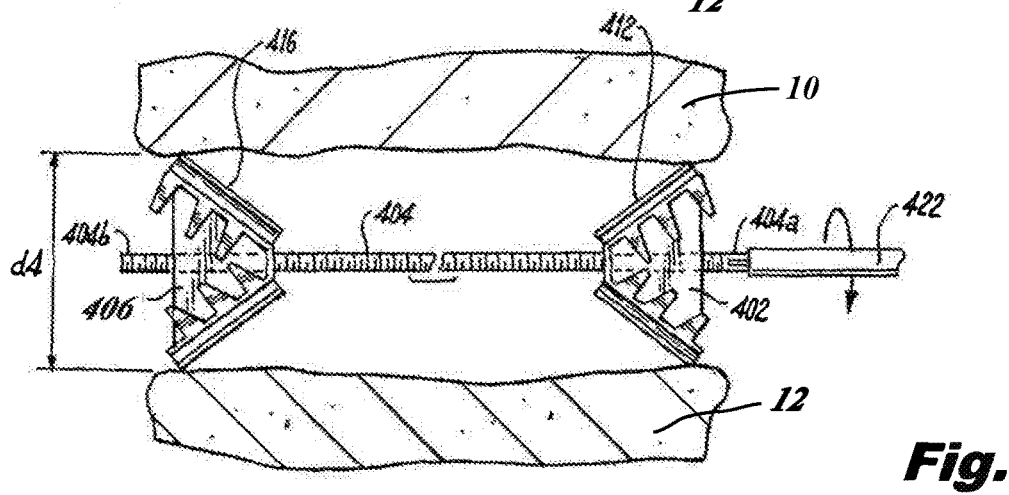
FIG. 10 is a cross-sectional view of the interbody spacer of FIG. 8, showing the spacer in an uncompressed state.

Referring now to FIGS. 8-10 another embodiment of a compressive spinal interbody spacer 400 in accordance with the present disclosure is shown. In this embodiment, the spacer 400 includes an elongated threaded shaft 404 having a first end 404a and an opposing second end 404b. A first spring loaded ramp 412 is positioned near the first end 404a on the shaft 404 and a second spring loaded ramp 416 is positioned near the second end 404b on the shaft 404. The spring loaded features 420, 422 of the ramps are shown schematically, but those skilled in the art will understand the configuration and number of spring features can vary without departing from the scope of the invention.

As best in FIG. 9, the spring loaded ramps 412, 416 are implanted between adjacent vertebrae 10, 12 such that the spring features 420, 422 maintain a minimum distance d3 between bone 10, 12 of the spine. With reference to FIG. 10, a first driving wedge 402 is configured to be threadably engaged with the first end 404a of the shaft 404 through threaded bore 408. A second driving wedge 406 is configured to be threadably engaged with the second end 404b of the shaft 404 through threaded bore 410. The first and second driving wedges 402, 406 are designed and configured to drive the first and second spring loaded ramps 412, 416 to maintain a maximum distance d4 between bone 10, 12 of the spine.

It is envisioned that while the first and second driving wedges 402, 406 are positioned such that the spacer 300 is set to a maximum distance, the spring loaded ramps 412, 416 help to deflect the compressive forces from the spine onto the first and second wedges 402, 406. In doing so, the spacer 300 is able to maintain its position and, as in the previous embodiment, the compressive force on the spine is evenly distributed across the spacer 300 to reduce pain and further damage.

While the apparatuses and methods of subject invention have been shown and described with reference to preferred embodiments, it is to be understood that any feature described in connection with one embodiment can be advantageously applied to other embodiments of the invention, even if not explicitly described in connection therewith, if such feature(s) are not mutually exclusive with other features of such embodiment. Nevertheless, those skilled in the art will readily appreciate that further changes or modifications may be made to devices and methods of the present invention without departing from the spirit and scope thereof. It is also to be appreciated that the following claims can be rearranged, combined, combined with other features disclosed herein, presented in multiple dependent form and the like.

What is claimed is:

1. An interbody spacer for a spine, comprising:
    a body having an upper surface and a lower surface, each of the upper surface and the lower surface configured to engage with a bone of the spine;
    a gripping member positioned within an interior passage of the body,
    said gripping member having a base and at least one arm,
    said at least one arm having a proximal end extending from the base and a distal end configured to extend from the upper surface or the lower surface of the body; and
    a compression spring cooperatively engaged with the gripping member,
    wherein the compression spring comprises a longitudinal axis that is parallel to the upper surface and the lower surface of the body, and
    wherein the distal end of the at least one arm extends past the upper surface or the lower surface of the body when the compression spring is in a compressed state.

2. The interbody spacer of claim 1, wherein the distal end of the at least one arm retracts within the interior passage of the body when the compression spring is in an uncompressed state.

3. The interbody spacer of claim 1, wherein the distal end of the at least one arm comprises teeth for gripping bone.

4. The interbody spacer of claim 1, wherein the at least one arm comprises a first arm and a second arm.

5. The interbody spacer of claim 4, wherein the interior passage of the body comprises:
    a central passage, a first upper passage having an opening on the upper surface of the body, and a second lower passage having an opening on the lower surface of the body.

6. The interbody spacer of claim 5, wherein the gripping member is Y shaped, the base of the gripping member positioned within the central passage of the body, the first arm positioned within the first upper passage, and the second arm positioned within the second lower passage.

7. The interbody spacer of claim 1, wherein the body further comprises an internal cavity configured to receive bone graft material.

8. A system for spinal surgery comprising:
an interbody spacer for a spine, comprising:
a body having an upper surface and a lower surface, each of the upper surface and the lower surface configured to engage with a bone of the spine;
a gripping member positioned within an interior passage of the body,
said gripping member having a base and at least one arm,
said at least one arm having a proximal end extending from the base and a distal end configured to extend from the upper surface or the lower surface of the body; and
a compression spring cooperatively engaged with the gripping member,
wherein the compression spring comprises a longitudinal axis that is parallel to the upper surface and the lower surface of the body, and
wherein the distal end of the at least one arm extends past the upper surface or the lower surface of the body when the compression spring is in a compressed state; and
an insertion instrument for inserting the interbody spacer into a patient.

9. The system of claim 8, wherein the base of said gripping member comprises a bore; and
said insertion instrument comprises a shaft having a distal end configured to be received within the bore of the gripping member,
wherein the distal end of the shaft is configured to push the gripping member distally to place the compression spring in the compressed state.

10. The system of claim 8, wherein the distal end of the at least one arm comprises teeth for gripping bone.

11. The system of claim 8, wherein the at least one arm comprises two arms forming a Y-shape.

12. The system of claim 8, wherein the interior passage comprises a central passage, a first upper passage having an opening on the upper surface of the body, and a second lower passage having an opening on the lower surface of the body.

13. The system of claim 12,
wherein the at least one arm comprises a first arm and a second arm, and
wherein the gripping member is Y-shaped, said base of the gripping member positioned within the central passage of the body, the first arm positioned within the first upper passage, and the second arm positioned within the second lower passage.

14. The system of claim 12, wherein the body further comprises an internal cavity configured to receive bone graft material.

15. A method of inserting an interbody spacer into a spine of a patient, comprising:
providing an interbody spacer comprising:
a body having an upper surface and a lower surface, each of the upper surface and the lower surface configured to engage with a bone of the spine;
a gripping member positioned within an interior passage of the body,
said gripping member having a base and at least one arm,
said at least one arm having a proximal end extending from the base and a distal end configured to extend from the upper surface or the lower surface of the body; and
a compression spring cooperatively engaged with the gripping member,
wherein the compression spring comprises a longitudinal axis that is parallel to the upper surface and the lower surface of the body;
inserting the interbody spacer into the patient with the compression spring in an uncompressed state;
inserting an insertion instrument into the interior passage of the body to contact the base of the gripping member; and
pushing a distal end of the insertion instrument to compress the compression spring and extend the distal end of the at least one arm out of the interior passage of the body.

16. The method of claim 15, wherein the distal end of the at least one arm comprises teeth, further comprising:
gripping the bone with the teeth when the at least one arm is extended.

17. The method of claim 16, wherein after insertion, the compression spring returns to the uncompressed state over time, thereby pulling the bone towards the interbody spacer.

18. The method of claim 15, wherein a proximal side of the base of said gripping member comprises a bore, and said insertion instrument comprises a shaft having a distal end, said method further comprising:
receiving the distal end of the shaft of the insertion instrument within the bore of the gripping member.

19. The method of claim 15, wherein the at least one arm of the gripping member comprises a first arm and a second arm forming a Y shape,
wherein the interior passage comprises a central passage receiving the base therein, a first upper passage having an opening on the upper surface of the body and receiving the first arm therein, and a second lower passage having an opening on the lower surface of the body and receiving the second arm therein,
the method further comprising:
extending the distal end of the first arm through the opening on the upper surface, and extending the distal end of the second arm through the opening on the lower surface when the compression spring is compressed.

20. The method of claim 15, wherein the body further comprises an internal cavity, the method further comprising:
inserting bone graft material into the internal cavity before inserting the interbody spacer into the patient.

* * * * *